(12) United States Patent
Poo et al.

(10) Patent No.: US 8,388,525 B2
(45) Date of Patent: Mar. 5, 2013

(54) ATRIAL LIFT RETRACTOR

(75) Inventors: Ramon E. Poo, Miami, FL (US); Joseph Lamelas, Miami, FL (US)

(73) Assignee: Miami Instruments LLC, Coral Gables, FL (US)

( * ) Notice: Subject to any disclaimer, the term of this patent is extended or adjusted under 35 U.S.C. 154(b) by 357 days.

(21) Appl. No.: 12/634,344

(22) Filed: Dec. 9, 2009

(65) Prior Publication Data

US 2011/0137128 A1    Jun. 9, 2011

(51) Int. Cl.
*A61B 1/32* (2006.01)

(52) U.S. Cl. ......... 600/206; 600/208; 600/210; 600/213

(58) Field of Classification Search .................. 600/206, 600/208, 210, 213, 214, 218, 219
See application file for complete search history.

(56) References Cited

U.S. PATENT DOCUMENTS

| 6,524,320 B2 * | 2/2003 | DiPoto ........................... 606/108 |
| 7,651,465 B1 * | 1/2010 | Sperling et al. ............... 600/219 |
| 2003/0195392 A1 | 10/2003 | Hamel et al. |
| 2006/0004261 A1 | 1/2006 | Douglas |
| 2007/0038032 A1 | 2/2007 | De Canniere et al. |
| 2008/0108876 A1 | 5/2008 | Houser et al. |

FOREIGN PATENT DOCUMENTS

| WO | WO2007/075903 A2 | 7/2007 |
| WO | WO2008/098616 A1 | 8/2008 |

* cited by examiner

*Primary Examiner* — Andrew Yang
*Assistant Examiner* — Olivia C Chang
(74) *Attorney, Agent, or Firm* — Novak Druce Connolly Bove + Quigg LLP

(57) ABSTRACT

A retractor includes a retractor support and an elongated retractor blade. The retractor blade has a first, closed position in which ends of the blade are positioned proximal to the support and a second, open position in which ends of the blade are positioned distal to the support. The retractor support has structure for engaging the retractor blade. A handle extends from the retractor support. A method of retracting tissue is also disclosed.

18 Claims, 22 Drawing Sheets

ATRIAL LIFT RETRACTOR

BACKGROUND OF THE INVENTION

The retraction of tissue during surgery and other medical procedures is particularly difficult where the tissue that must be retracted is deep tissue or organs where there is limited space in which to position retraction devices. One such medical procedure is the repair or replacement of heart valves. In the case of procedures involving the mitral valve or the tricuspid valve, the valve is usually accessed through an incision in the wall of the heart at the left atrium in the case of the mitral valve, or the right atrium in the case of the tricuspid valve. The tissue surrounding this incision is retracted to enable the surgeon to reach the valve, and the tissue forming the wall of the atrium must also be retracted to prevent the walls of the atrium from closing in and obstructing the valve. Retraction devices are frequently large and unwieldy when working in close quarters such as during open heart surgery.

SUMMARY OF THE INVENTION

A retractor includes a retractor support and an elongated retractor blade. The retractor blade has a first, closed position in which ends of the blade are positioned proximal to the support and a second, open position in which ends of the blade are positioned distal to the support. The retractor support has structure for engaging the retractor blade. A handle extending from the retractor support is also provided.

The retractor blade can be detachable from the support. The retractor support can have a slot for receiving the retractor blade. The retractor support can have an engagement surface and the retractor blade can have a notch for receiving the engagement surface.

The blade can be connected to the retractor support by hinges. The blade can have a plurality of blade segments, at least one blade segment being pivotally connected to each lateral side of the support. At least one blade segment can be pivotally attached to another blade segment. The pivotal attachment can be provided by hinges.

The blade can comprise a shape memory material. The shape memory material positions the blade in the closed position at room temperature, and moves the blade to the open position when the shape memory material is heated. The blade can comprise a blade body and the shape memory material can be provided as strips connected to the blade body. The blade can comprise a blade body and the shape memory material can be provided as a sheet connected to the blade body.

The handle can be detachable from the support. The retractor support and the handle can have a gas conduit for conducting a gas from the handle to the retractor support. The support has a gas outlet port for releasing the gas to a surgical site at the support.

The retractor can have actuating structure for moving the blade from the closed position to the open position. The actuating structure can comprise biasing structure. The biasing can comprise at least one spring.

The retractor can comprise locking structure for locking the blade in the closed position. The locking structure can be releasable to permit the biasing to move the blade to the open position.

The blade has a long dimension and a short dimension. The long dimension can be at least twice the length of the shorter dimension.

A method for retracting tissue about an opening includes the steps of: inserting a retractor support into the opening; attaching a retractor blade, where the retractor blade is in a closed position in which ends of the blade are positioned proximal to the support; and moving the blade to an open position in which ends of the blade are positioned distal to the support. The method can further comprise the step of attaching a handle to the retractor support.

The method can comprise the step of removing the retractor blade from the support and from the opening, and then removing the handle from the support and then removing the support from the opening. The opening is in the wall of an atrium and the retractor support and retractor blade are positioned in the atrium.

BRIEF DESCRIPTION OF THE DRAWINGS

There are shown in the drawings embodiments that are presently preferred it being understood, however, that the invention is not limited to the precise arrangements and instrumentalities shown, wherein.

DETAILED DESCRIPTION OF THE INVENTION

There is shown in FIGS. 1-6 a tissue retractor 20 according to the invention. The tissue retractor 20 has a retractor support 24, a handle 30, and a retractor blade 36. The retractor blade has a first, closed position shown in FIG. 6 and a second, open position shown in FIG. 3. The tissue retractor 20 has closing structure for maintaining the blade 36 in the closed position so that the blade can be inserted through an incision or opening. The tissue retractor also has opening structure for opening the blade when the blade has been properly positioned in the atrium or other confined space in the body. The retractor blade 36 can be formed integrally with the retractor support 24, can be connected to the support 24, or can be detachable with respect to the support 24.

Figure 5:
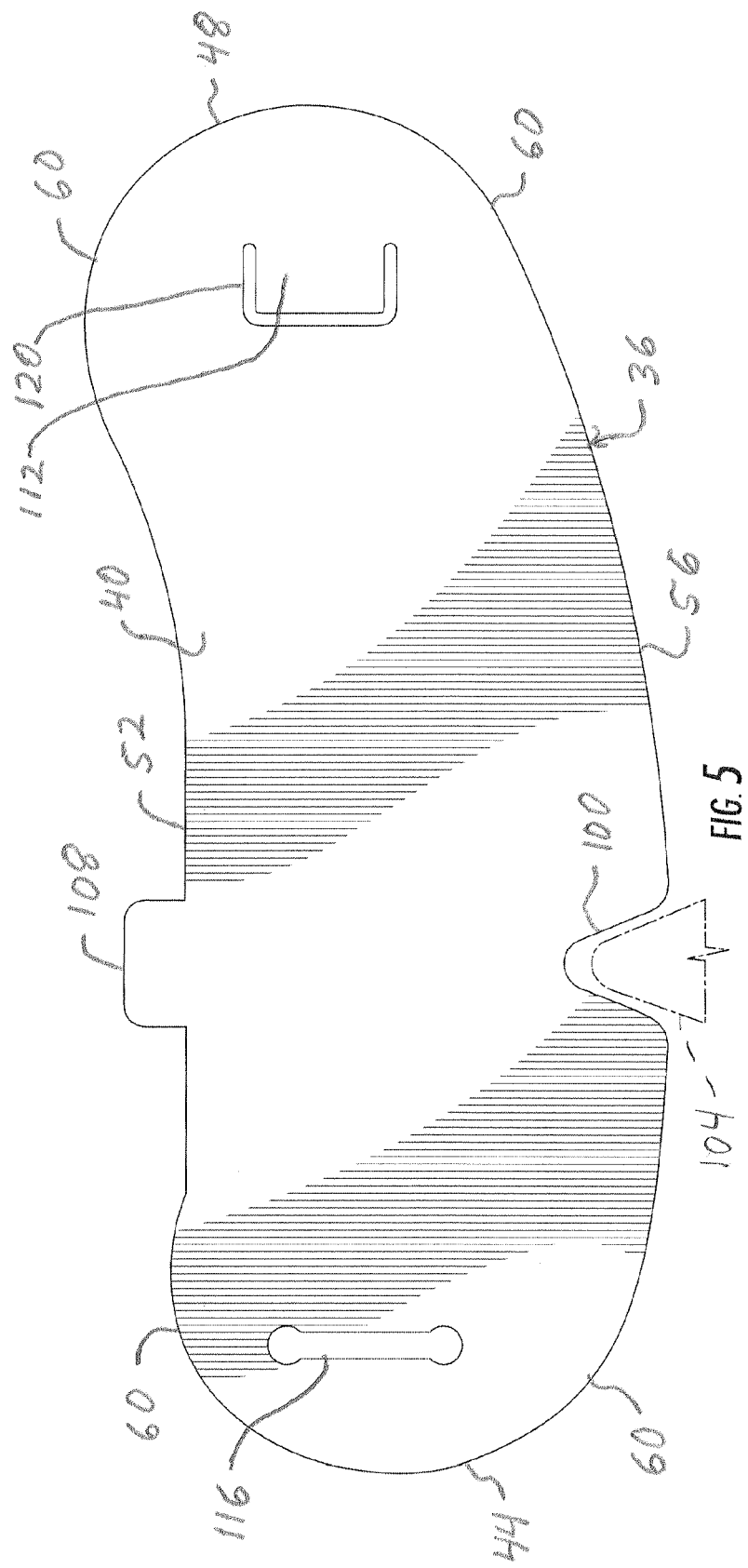
FIG. 5 is a front elevation of a retractor blade.

As shown in FIG. 5, in one embodiment the retractor blade 36 is in the form of a substantially rectangular, elongated, and planar body 40. The body 40 has a first short side 44 and a second short side 48, and a first long side 52 and a second long side 56. The dimensions and shape of the blade 36 can vary. In one embodiment, the dimension of the long sides 52 and 56 is at least twice the dimension of the short sides 44 and 48. The thickness of the planar body can vary depending on the material used to make the body 40 and the particular intended application, but in one aspect can be between 0.25 mm and 1 mm. The corners 60 between the long sides and the short sides can be rounded to minimized cutting or abrading of tissues by sharp corners.

Figure 1:
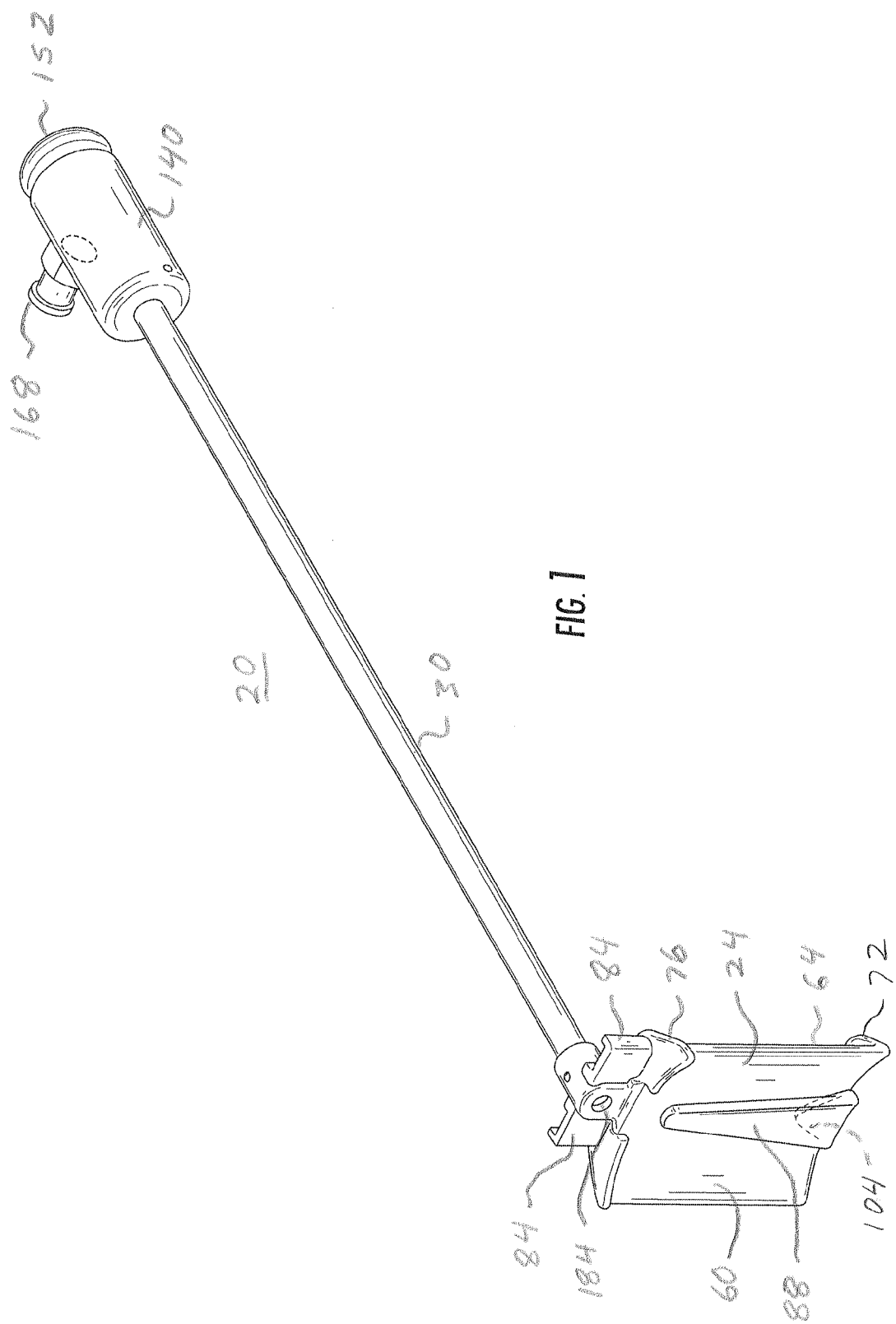
FIG. 1 is a perspective view of an atrial lift retractor according to the invention.
Figure 2:
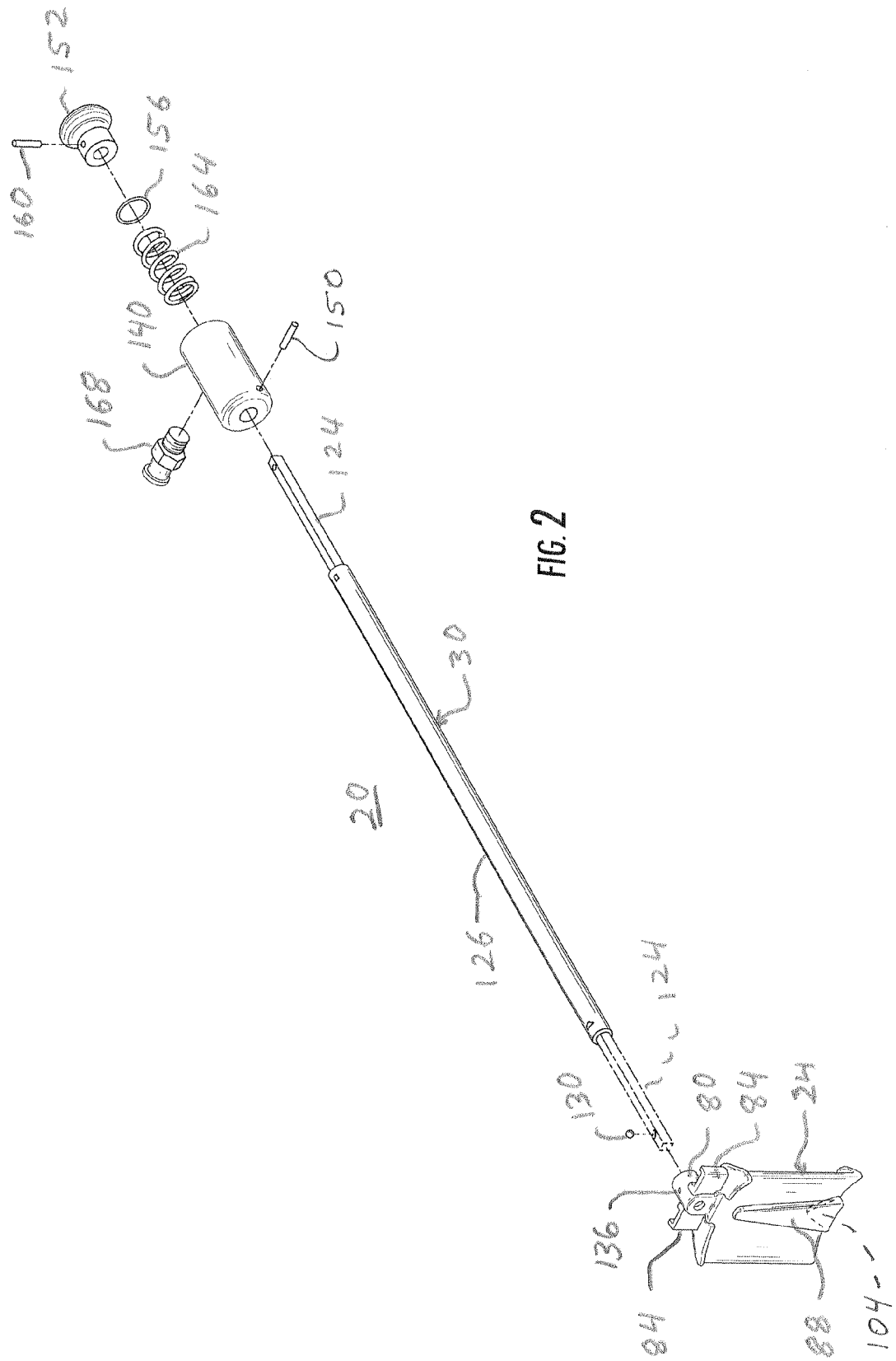
FIG. 2 is an exploded perspective view of an atrial lift retractor according to the invention, partially in phantom.
Figure 3:
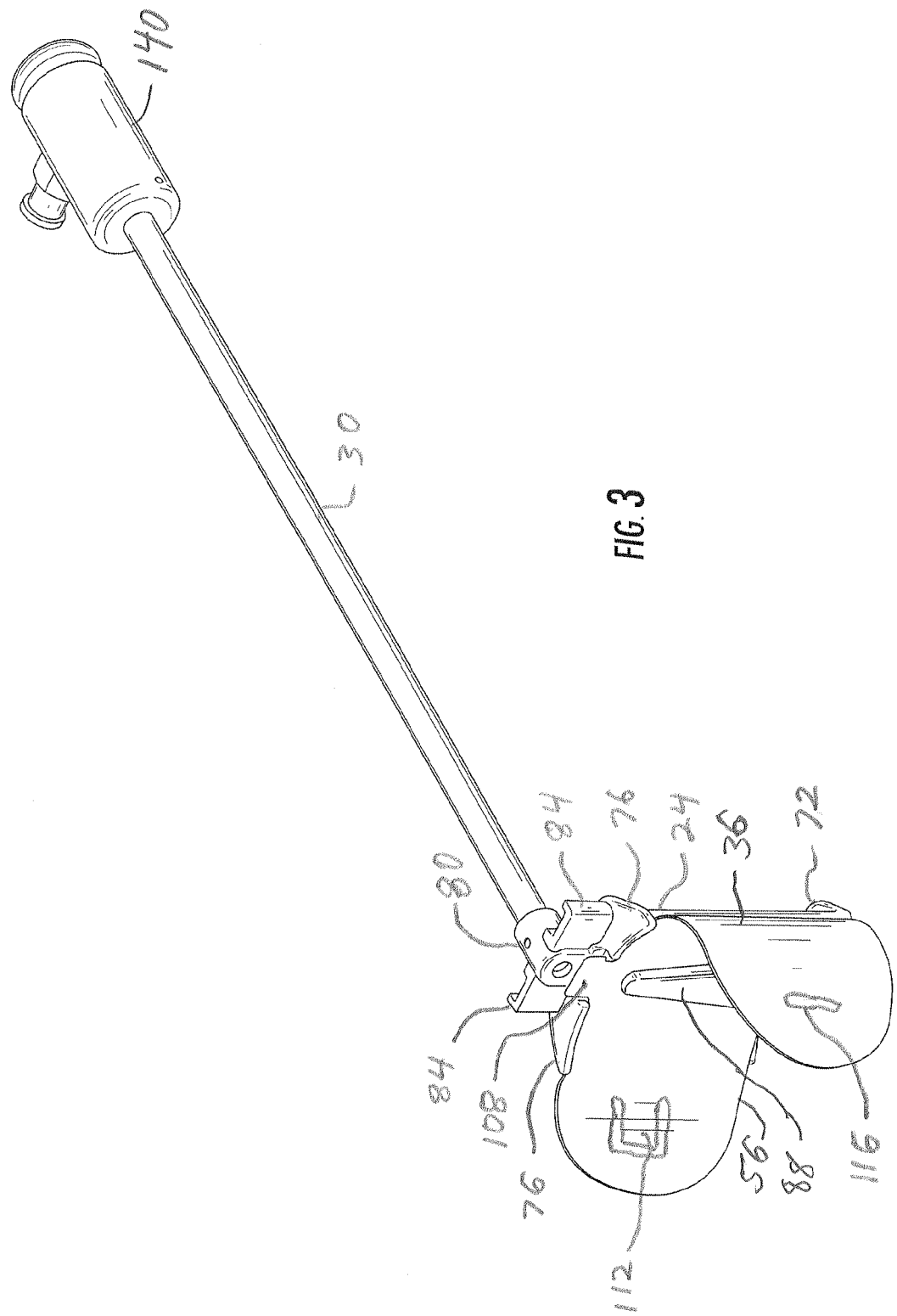
FIG. 3 is a perspective view of an atrial lift retractor with a retractor blade.
Figure 4:
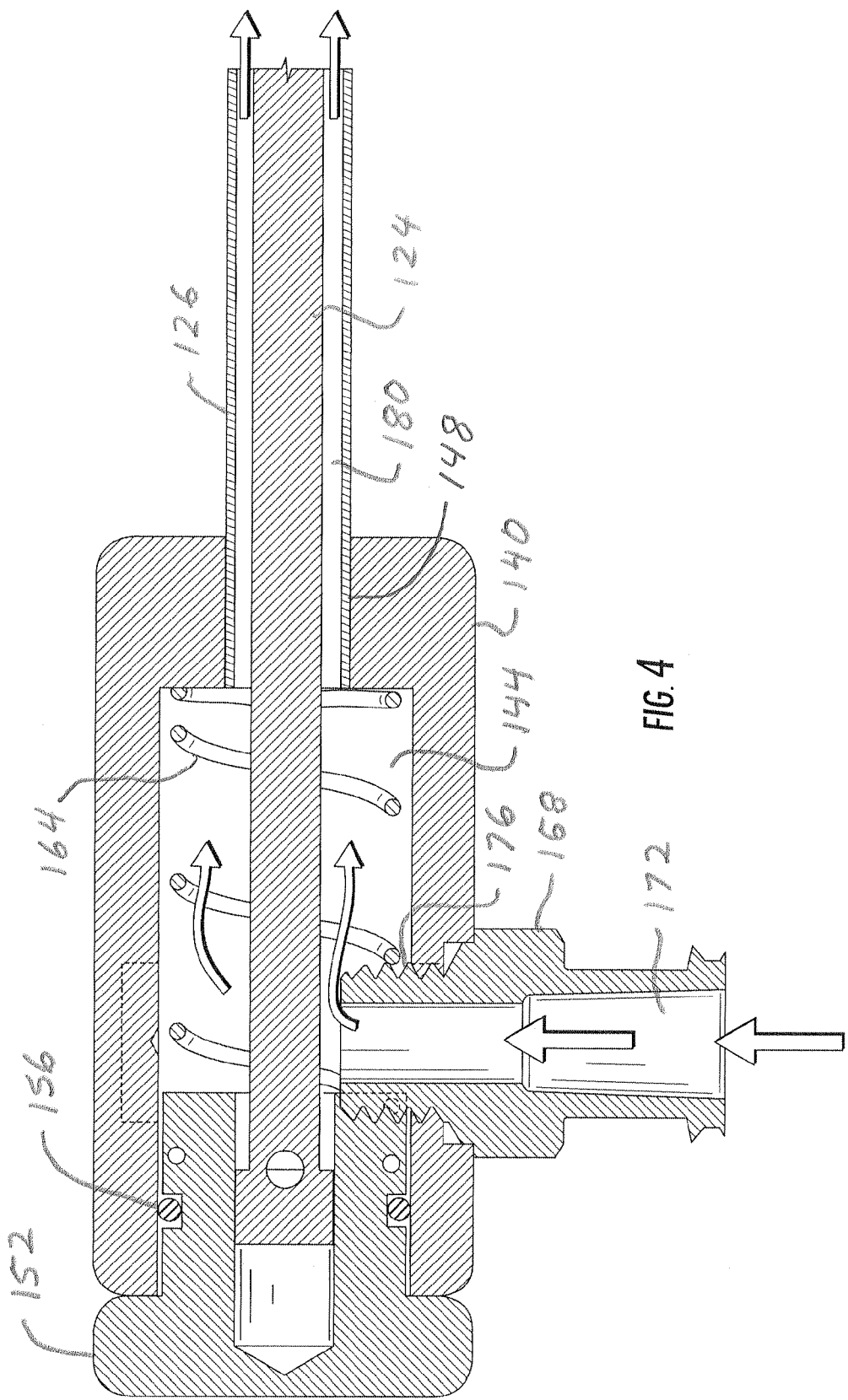
FIG. 4 is a cross section of a handle of the atrial lift retractor depicting gas flow through the handle.

The material used to construct the blade 36 can be any suitable material such as a medical grade metal or plastic material. The material can be flexible so that the blade 36 can be deformed to the closed position (FIG. 6), and then will expand under its own biasing to the open position (FIG. 3). An external biasing such as a leaf spring or an actuator can alternatively be provided to move the blade to the open position.

The retractor support 24 is connected to or detachably connects to the retractor blade 36. In the embodiment shown in FIGS. 1-6, the support 24 has a substantially concave front face 60 and a convex rear face 64. Other configurations are possible. A ledge portion 72 can comprise a lip or flange and provides a surface which retards removal of the support 24 through the incision and helps to keep the support in place in the body. Upper flanges 76 can be provided to engage the blade 36 to help to secure the blade against removal from the support 24. The support 24 can have a fitting 80 for attachment of the support to a handle. Side braces 84 can be provided to provide a surface to grip the support 24 with pliers or another tool, and can also serve to rigidify the retractor support 24.

The support 24 can have structure for engaging the blade 36. This structure can take many forms, including clips, pins, snaps and other engagement structure. In the embodiment of FIGS. 1-6, a slot member 88 can be provided. The slot member is provided on the front face 60 of the support 24 and is positioned such that a space or slot is created between the slot member 88 and the front face 60 of the support 24. The blade 36 is positioned in the slot and the long side 52 is placed under the upper flange 76 such that it will be retained in this position. The blade 36 can include features which allow the blade 36 to be fixed to the support 24 in the proper position. A lower notch 100 can be provided to engage a cooperatively shaped guide or engagement surface 104 (shown in phantom) on the support 24. The guide surface 104 can be part of a piece that joins the slot member 88 to the concave surface 60 of the support 24, and which creates the space or slot by means of spacing the slot member 88 from the concave surface 60. An upper notch 108 can be provided on the blade 36 and is designed to fit between the upper flanges 76 to assist in retaining the blade 36 in position on the support 24. This can be significant because in atrial retraction the positioning of the blade on the support 24 is not symmetrical—the short side 48 is positioned further from the support 24 in the open configuration than is the short side 44. This is due to the geometry of the atrium, and the geometry of the blade can change with the geometry of the tissue that must be retracted. It is an advantage of the invention that different retractions can be accomplished merely by changing the blade 36 to a blade with a geometry (size and shape) that is intended for a different retraction setting.

Figure 6:
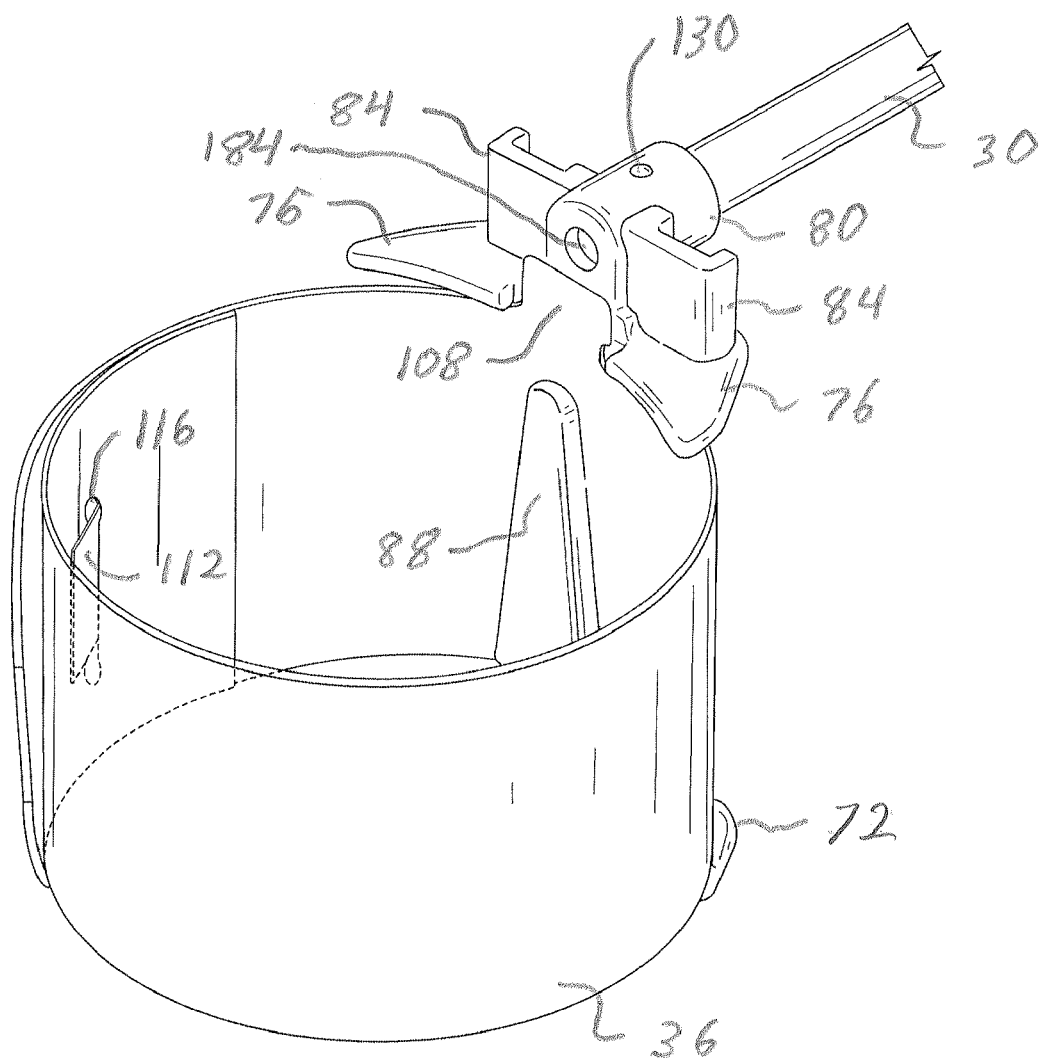
FIG. 6 is a perspective view of an atrial lift retractor with a retractor blade in a first mode of operation.

The blade 36 is in the closed position when inserted through the incision or opening (FIG. 6). Different designs and methods can be used to maintain the blade 36 in the closed position. In the embodiment shown in FIG. 5 a tab 112 is provided adjacent the short side 48 and a slot 116 is provided adjacent the short side 116. The tab 112 can be formed by creating a scribe or void 120 in the shape of the tab 112 so that the tab 112 is formed from the material of the body 40. The tab 112 can be positioned in the slot 116 to secure the blade 36 in the closed position. The blade 36 can be released to the open position by forcing the short side 44 and short side 48 apart, so as to separate the tab 112 from the slot 116. This can be accomplished by pliers, forceps, or other devices. Other methods and constructions for maintaining the blade 36 in the closed position are possible, including clips, snaps, fasteners, and others. Other means are also possible for moving the blade from the closed position to the open position, for example, mechanical actuators.

Figure 15:
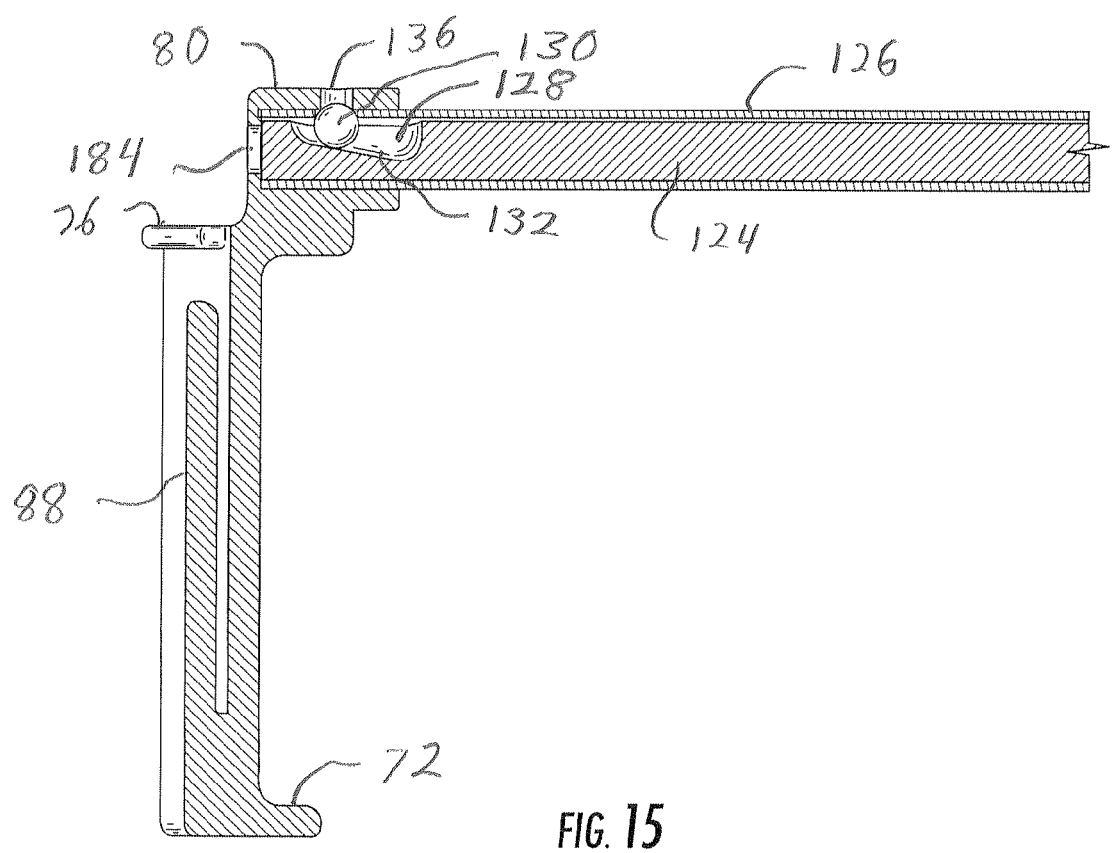
FIG. 15 is a cross section of the retractor support and distal portion of the handle.

The support 24 is preferably detachable from the handle 30. The structure for attaching the handle to the support can vary. In the embodiment shown in FIG. 2, the handle 30 comprises an elongated actuator 124 and a cover 126. An engagement member 130 is provided which in this embodiment is in the shape of a sphere 130. The engagement member 130 can be located on the actuator 124, which is extended from the cover 126 in phantom in FIG. 2 for clarity of viewing the sphere 130. A groove 128 can be formed in actuator 124 and provided with inclined surface 132 (FIG. 15). The engagement member 130 is adapted to engage cooperating structure in the fitting 80 such as opening 136 to prevent the removal of the handle 30 from the fitting 80 until removal of the retractor is desired. A corresponding opening can be provided in the cover 126 such that the sphere will protrude through the cover 126 and fitting 80 as shown in FIG. 6. Movement of the actuator 124 will allow the sphere 130 to drop as the inclined surface 132 moves past the sphere, out of engagement with the fitting 80 to permit release of the handle 30 from the support 24 (FIG. 15). Other means of detachably engaging the handle 30 to the support 24, such as cooperating male and female threads on the handle 30 and the support 24, are possible.

A grip 140 can be provided. The grip 140 has an interior opening 144 and a channel 148. Handle 30 can extend into the grip 140 through the channel 148 and can be secured by suitable structure such as pin 150. A push button 152 is slidably mounted in the open interior 144 of the grip 140. An o-ring seal 156 can be provided. The actuator 124 can be connected to the button 152 by suitable structure such as pin 160. A spring 164 or other suitable structure can provide biasing such that the actuator remains in a position securing the handle 30 to the fitting 80 until release of the handle 30 from the support 24 is desired. The button 152 can then be pressed, moving the actuator 124 and inclined surface 132 to permit the sphere 130 to drop and the handle to be released from the support 24.

Gases such as carbon dioxide are frequently used during cardiac procedures to flush the area of oxygen. The retractor 20 can also be used to provide for a flow of such gas. A gas fitting 168 with a gas inlet port 172 can be provided in the handle 30 such as at grip 140. Suitable connecting structure such as threads 176 can be provided to secure the gas fitting 168. An annular space 180 between the actuator 124 and cover 126 can communicate with the open interior 144. Gas can thereby flow through the port 172, open interior 144, and the annular space 180. The gas will exit through gas outlet port 184 in the fitting 80 to reach the surgical site.

Figure 7:
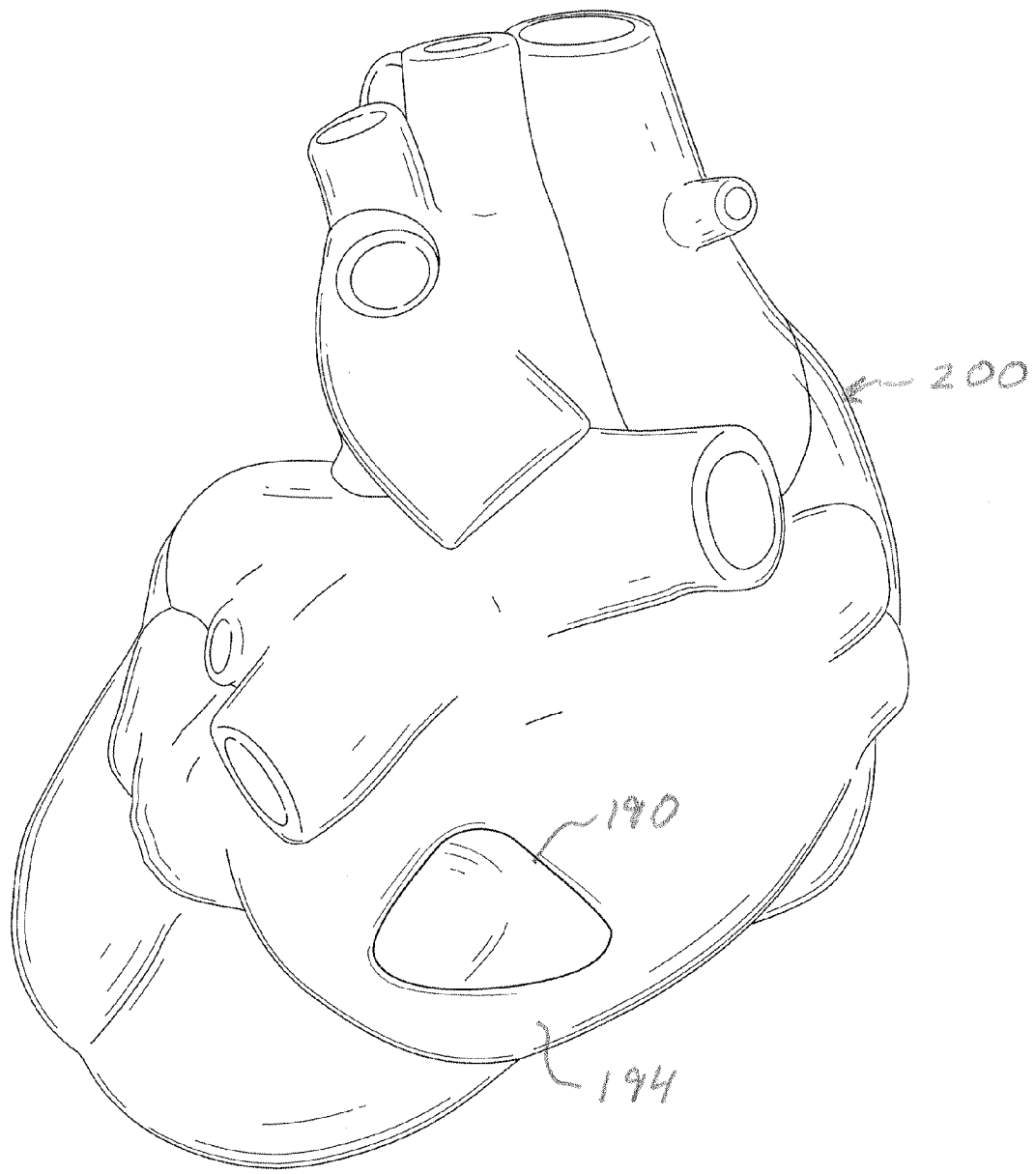
FIG. 7 is a perspective view of a heart, with an incision for accessing the left atrium.
Figure 8:
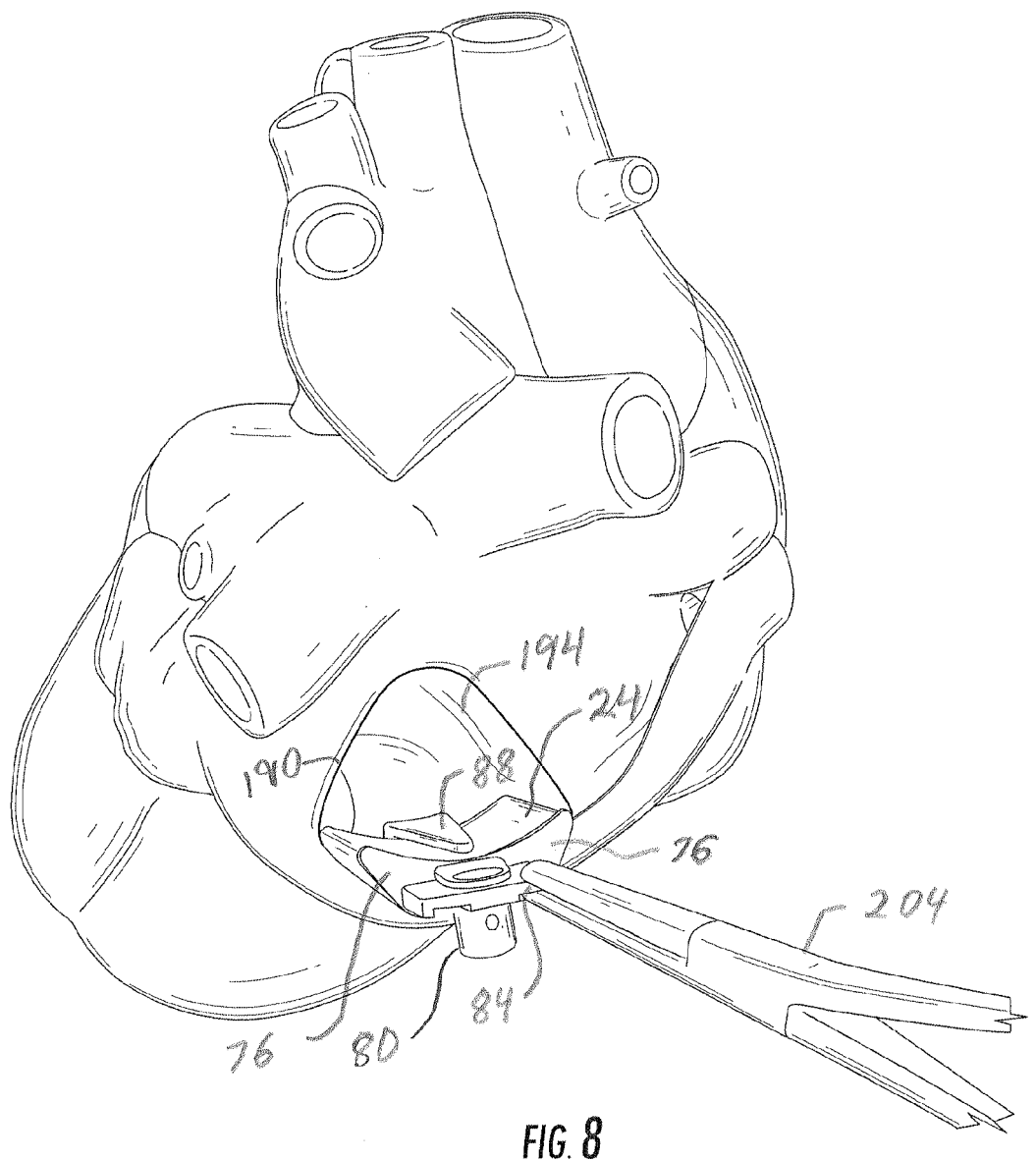
FIG. 8 is a perspective view of the insertion of the retractor support into the atrium.
Figure 9:
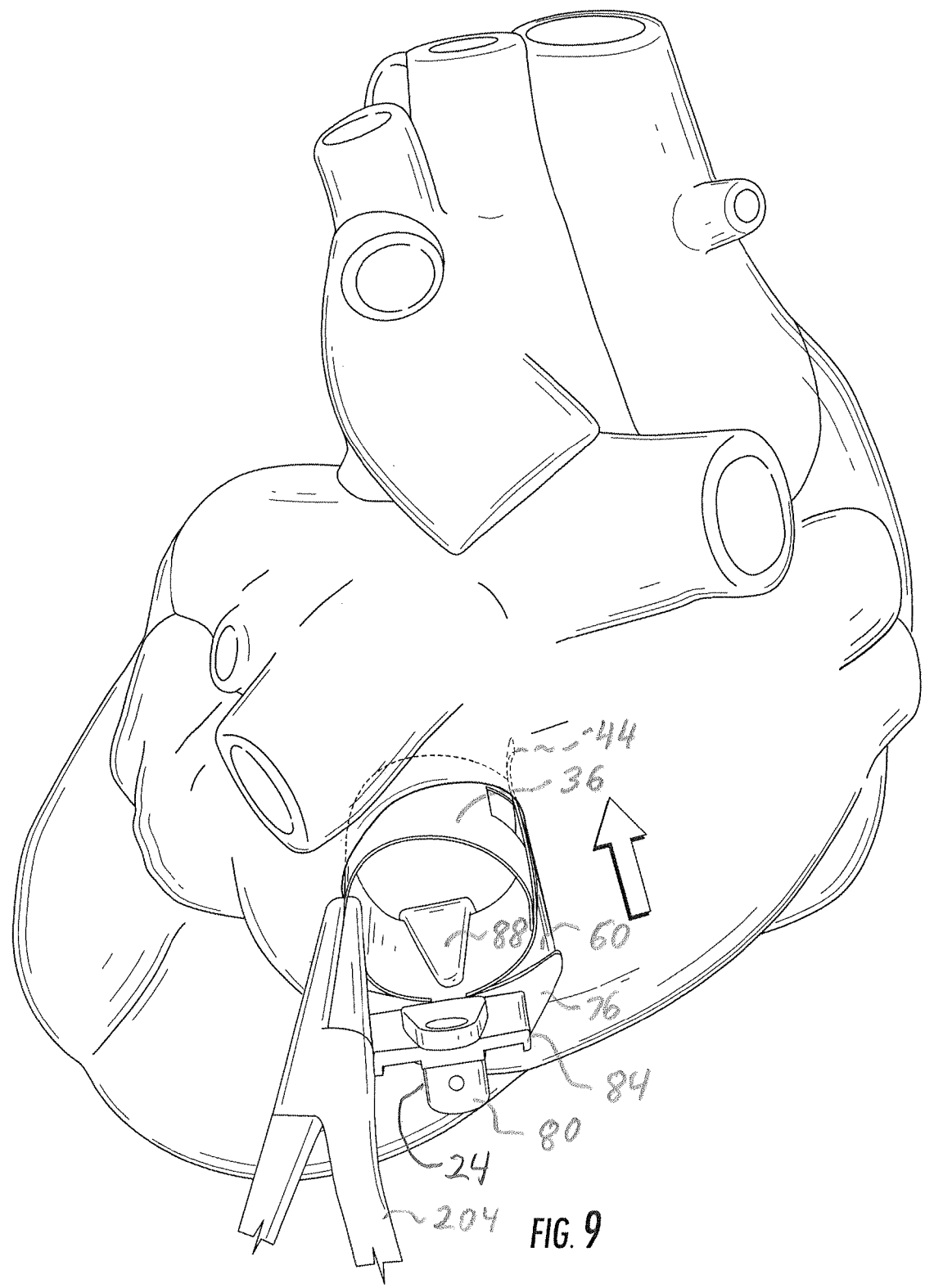
FIG. 9 is a perspective view of the attachment of the retractor blade to the retractor support.
Figure 10:
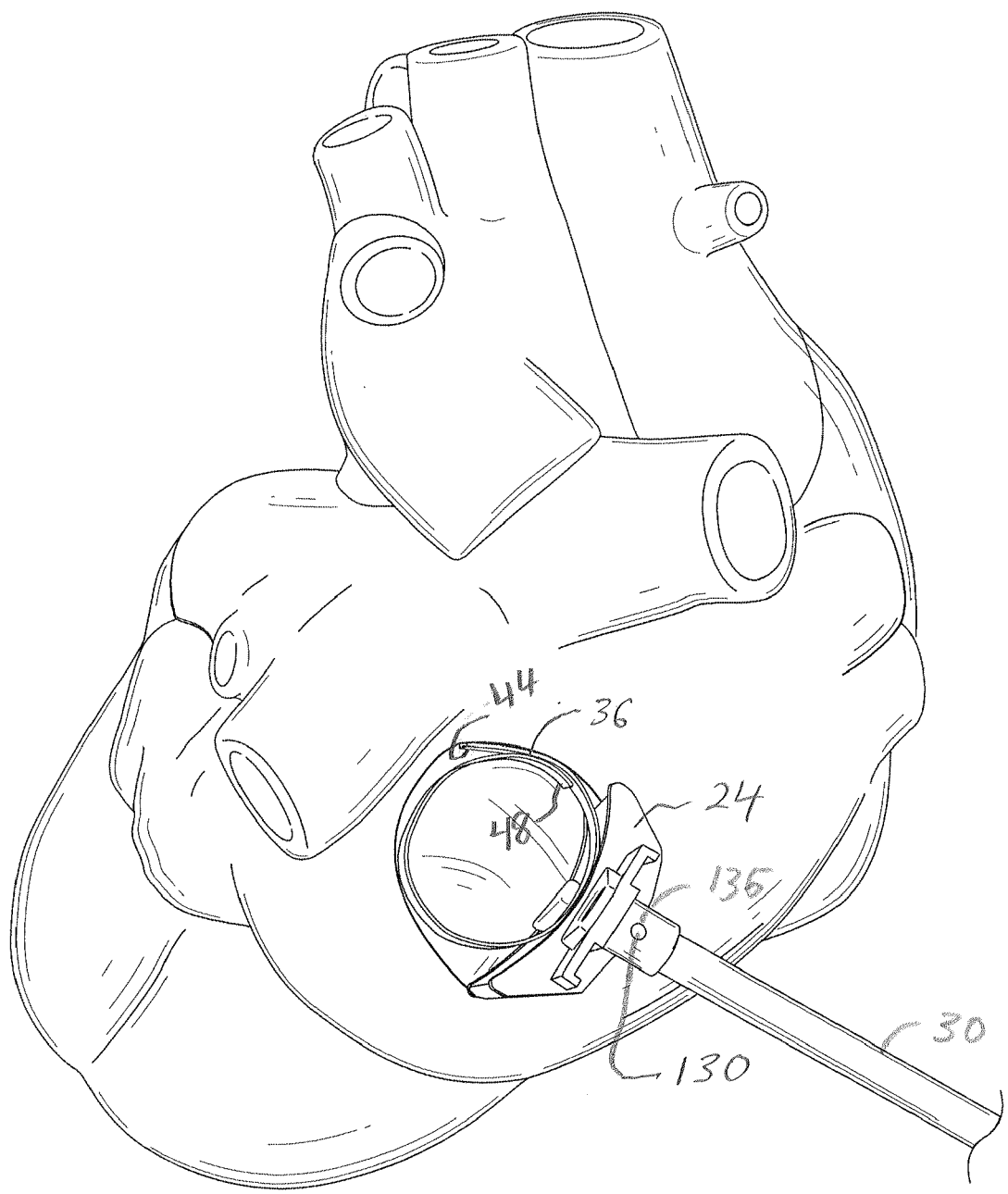
FIG. 10 is a perspective view of the attachment of a retractor handle to the retractor support.
Figure 11:
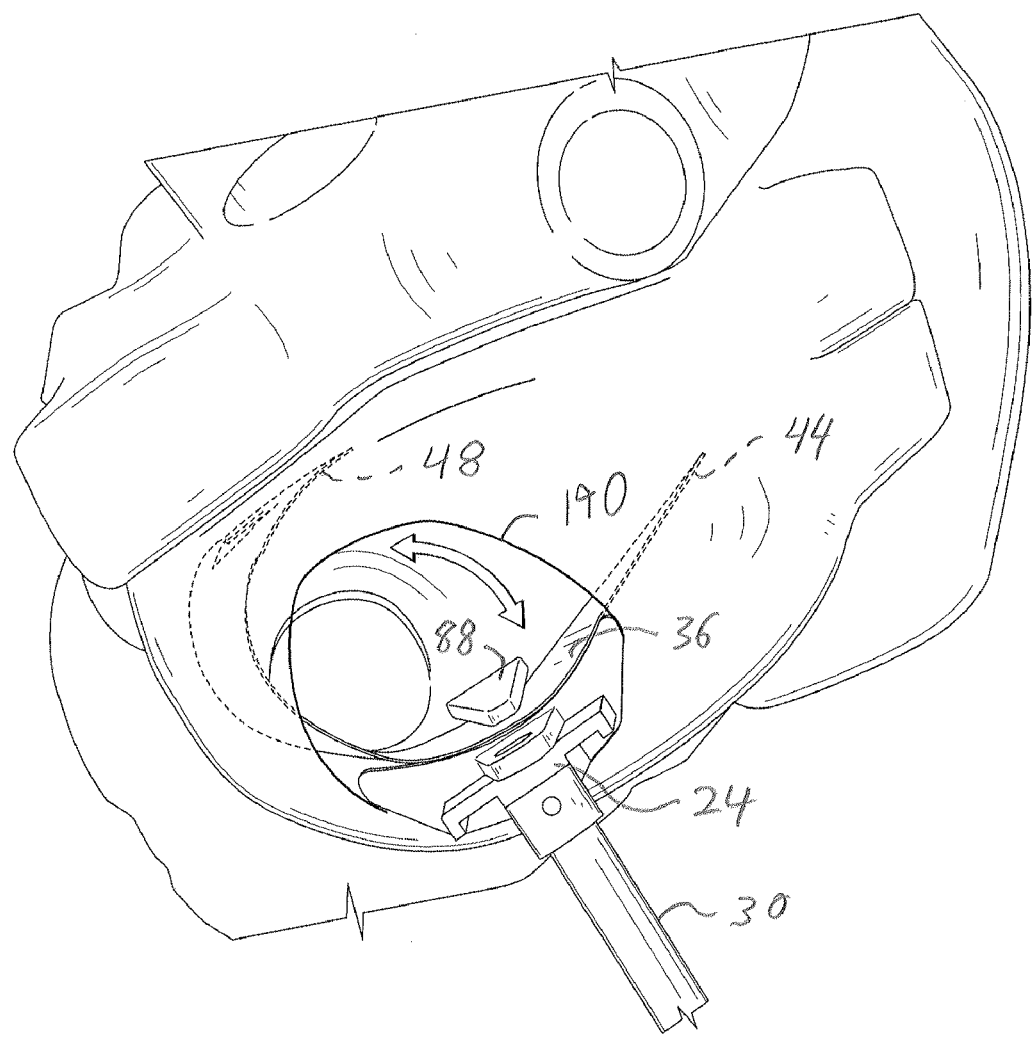
FIG. 11 is a perspective view of the opening of the retractor blade in the atrium.
Figure 12:
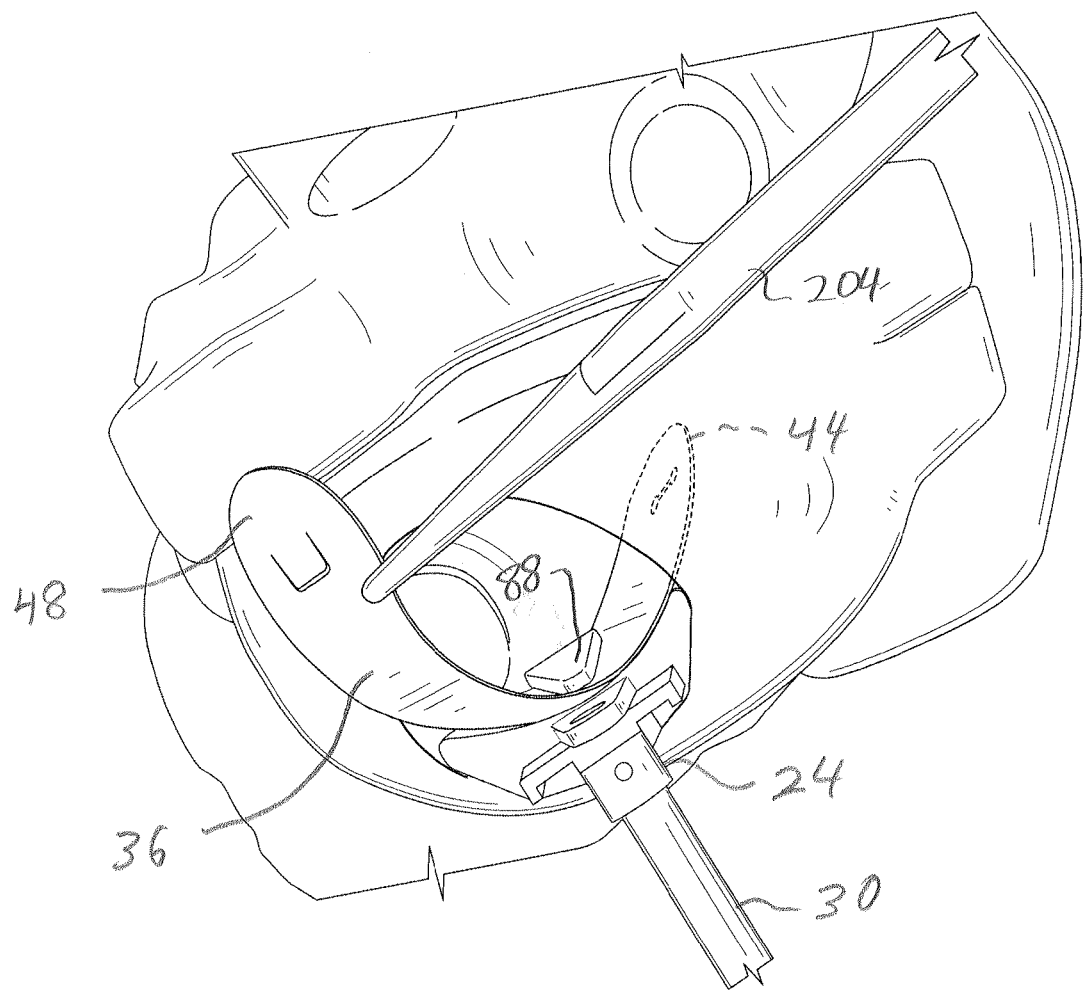
FIG. 12 is a perspective view of the removal of the retractor blade from the retractor support.
Figure 13:
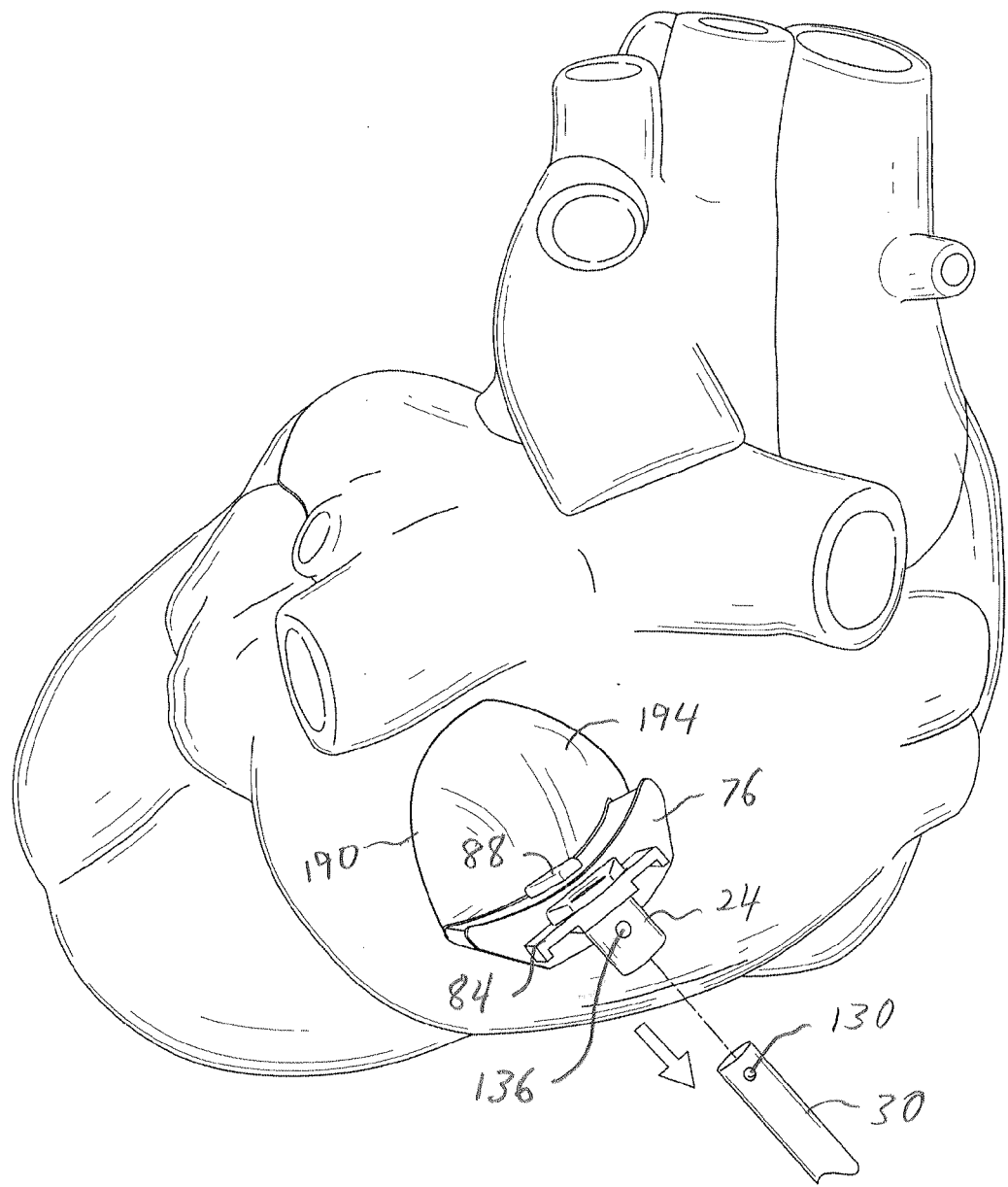
FIG. 13 is a perspective view of the removal of the retractor handle from the retractor support.
Figure 14:
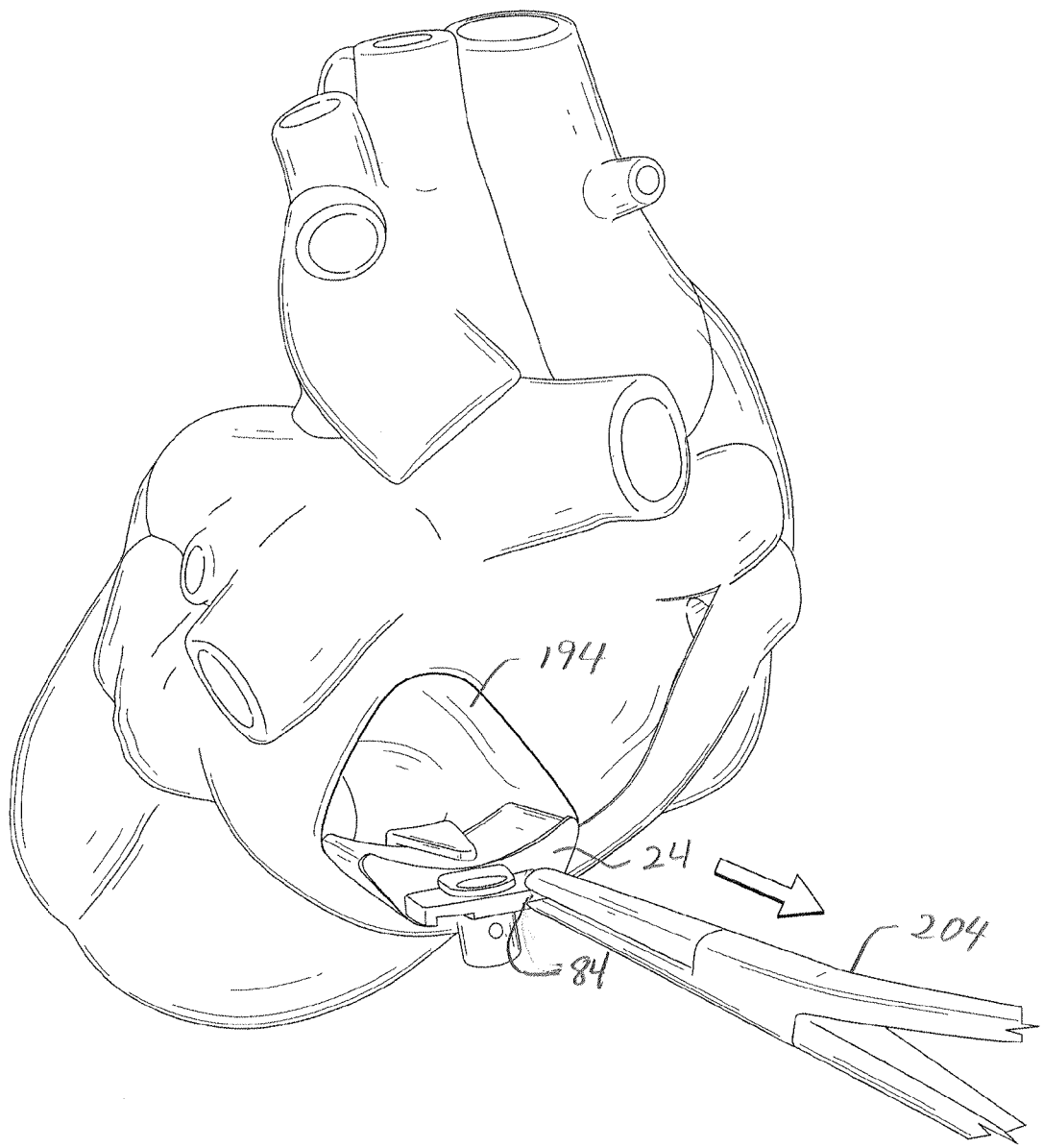
FIG. 14 is a perspective view of the removal of the retractor support from the atrium.

Operation of the retractor 20 is illustrated in FIGS. 7-15 in connection with heart valve surgery, although the invention has utility in many other forms of surgery. An incision is made through the chest and subsequently an incision 190 is made in the wall of the atrium 194 of the heart 200 (FIG. 7). Forceps 204 or another suitable device can be used to grasp the support 24, as at brace 84, to place the support 24 into the atrium 194 (FIG. 8). Forceps 204 are then used to attach the blade 36 to the support 24 by positioning the blade 36 between the slot member 88 and the concave surface 60 (FIG. 9). The blade 36 is in the closed position in which the ends 44, 48 are positioned proximal to the support 24. The handle 30 is then attached to the support 24 by inserting the actuator 124 into the fitting 80 until the sphere 130 is driven upward by the inclined surface 132 through the opening 136 in the fitting 80 (FIG. 10). An opening through the chest of the patient may be required to provide access of the handle 30 to the support 24. The forceps or another instrument is then used to release the blade 36, as by removing the tab 112 from the slot 116. The blade 36 will then move to the open position in which the ends 44, 48 are positioned distal to the support 24 (FIG. 11). The retractor blade 36 can be removed when desired by forceps 204 or other means (FIG. 12). The handle 30 can then be removed, such as by operation of the push button 152 on the actuator 124 (FIG. 13). The support 24 can then be removed by forceps 204 (FIG. 14).

An alternative embodiment of a retractor according to another aspect of the invention is shown in FIGS. 16-21. The retractor 220 includes a retractor support portion 224. The retractor blade in this embodiment is hinged to the support 224. Blade portions can also be hinged to each other. A first blade segment 230 can have hinge elements 234 that are joined to hinge elements 240 on the support 224. A second blade segment 244 can have hinge elements 250 connected to hinge elements 248 on the first blade segment 230. A third blade segment 258 can be provided on a side of the support 224 opposite to the first blade segment 230. The third blade segment 258 can have hinge elements 262 which connect to hinge elements 266 on the support 224. The support 224 can have a fitting 280 for attaching a handle (not shown), side braces 284, and upper flanges 276, and gas outlet port 290.

Figure 16:
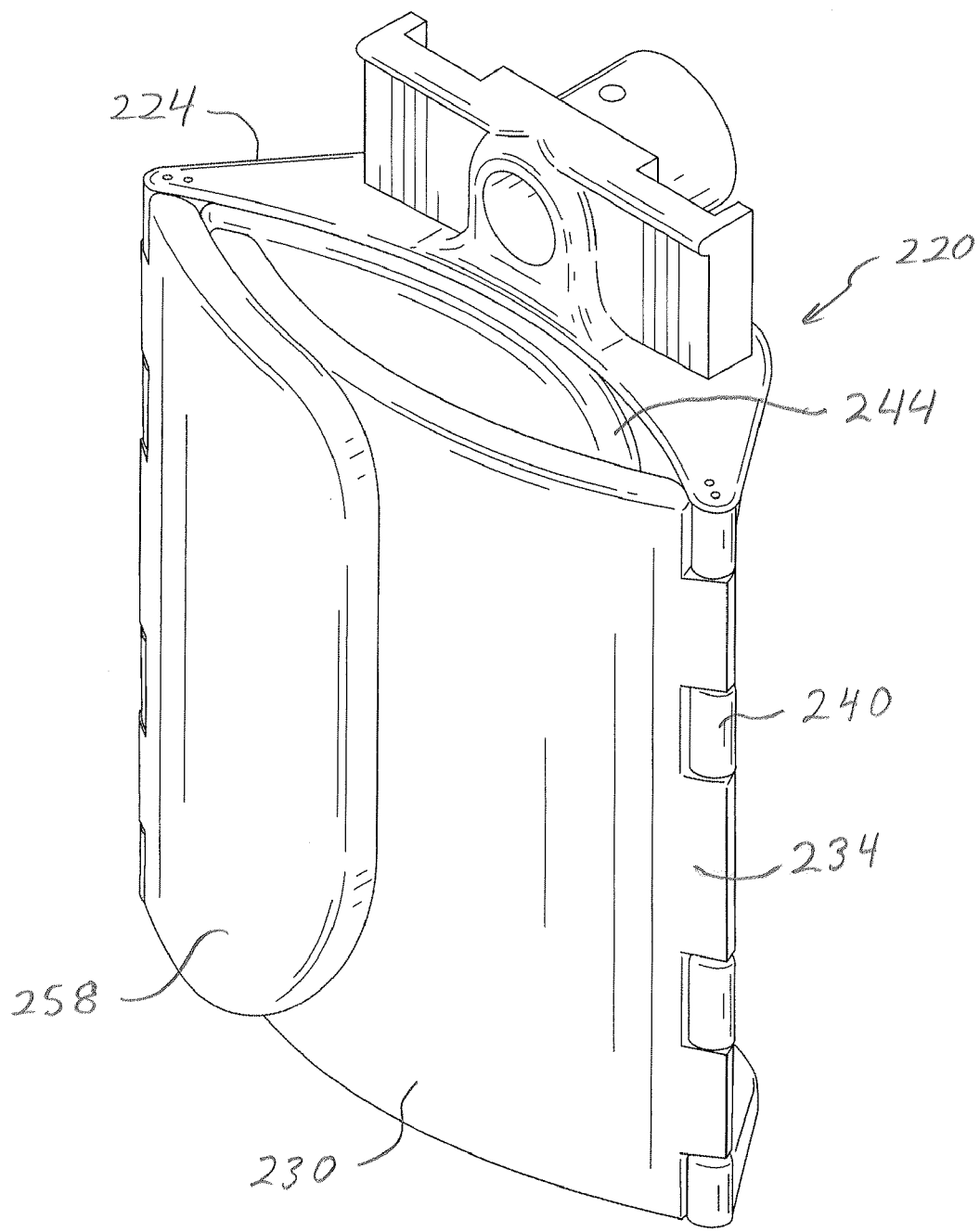
FIG. 16 is a perspective view of a retractor according to another embodiment of the invention, in a closed position.
Figure 17:
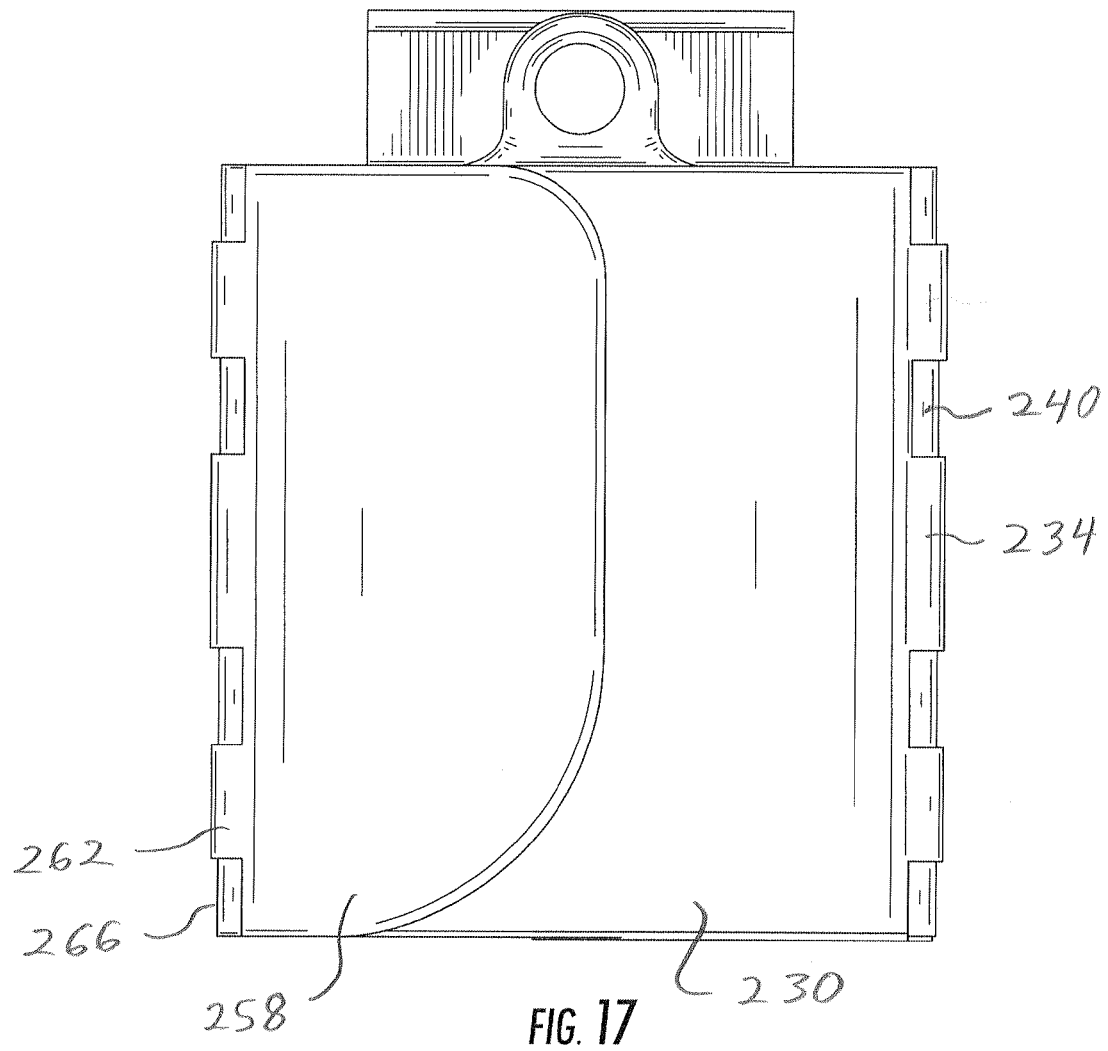
FIG. 17 is a front elevation.
Figure 18:
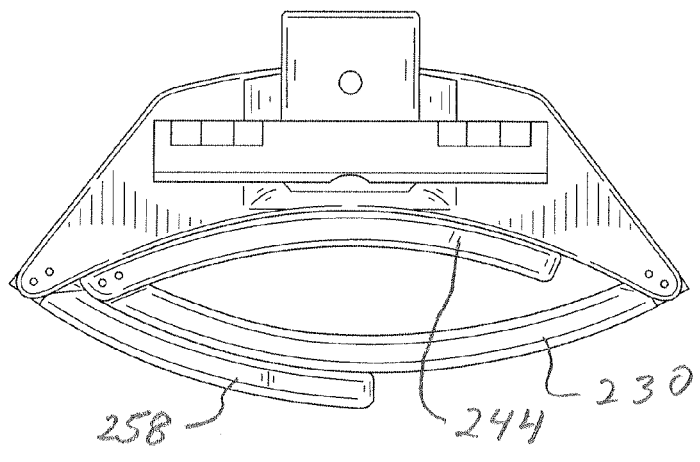
FIG. 18 is a top plan view.
Figure 19:
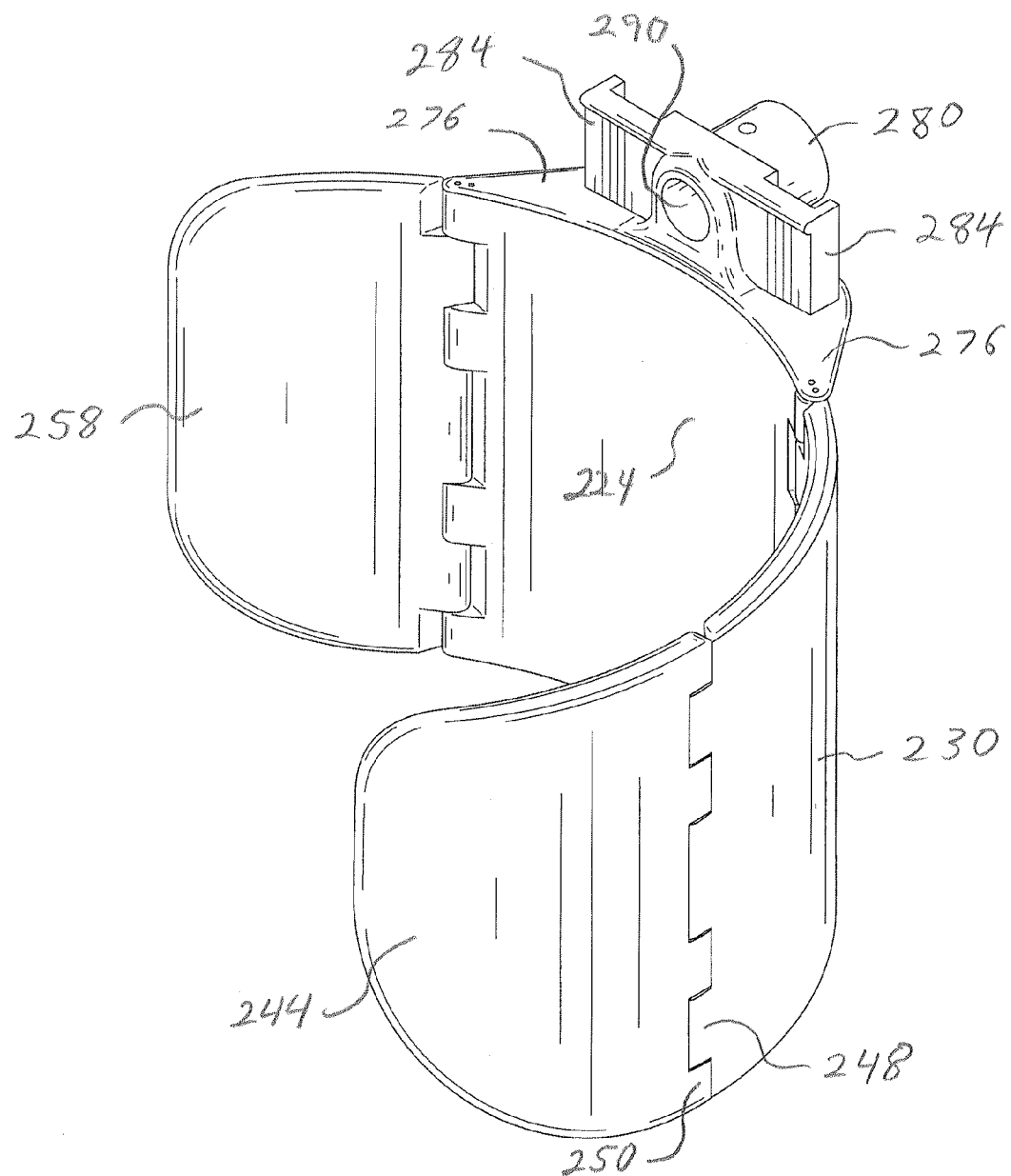
FIG. 19 is a perspective view of the retractor of FIG. 16, in an open position.
Figure 20:
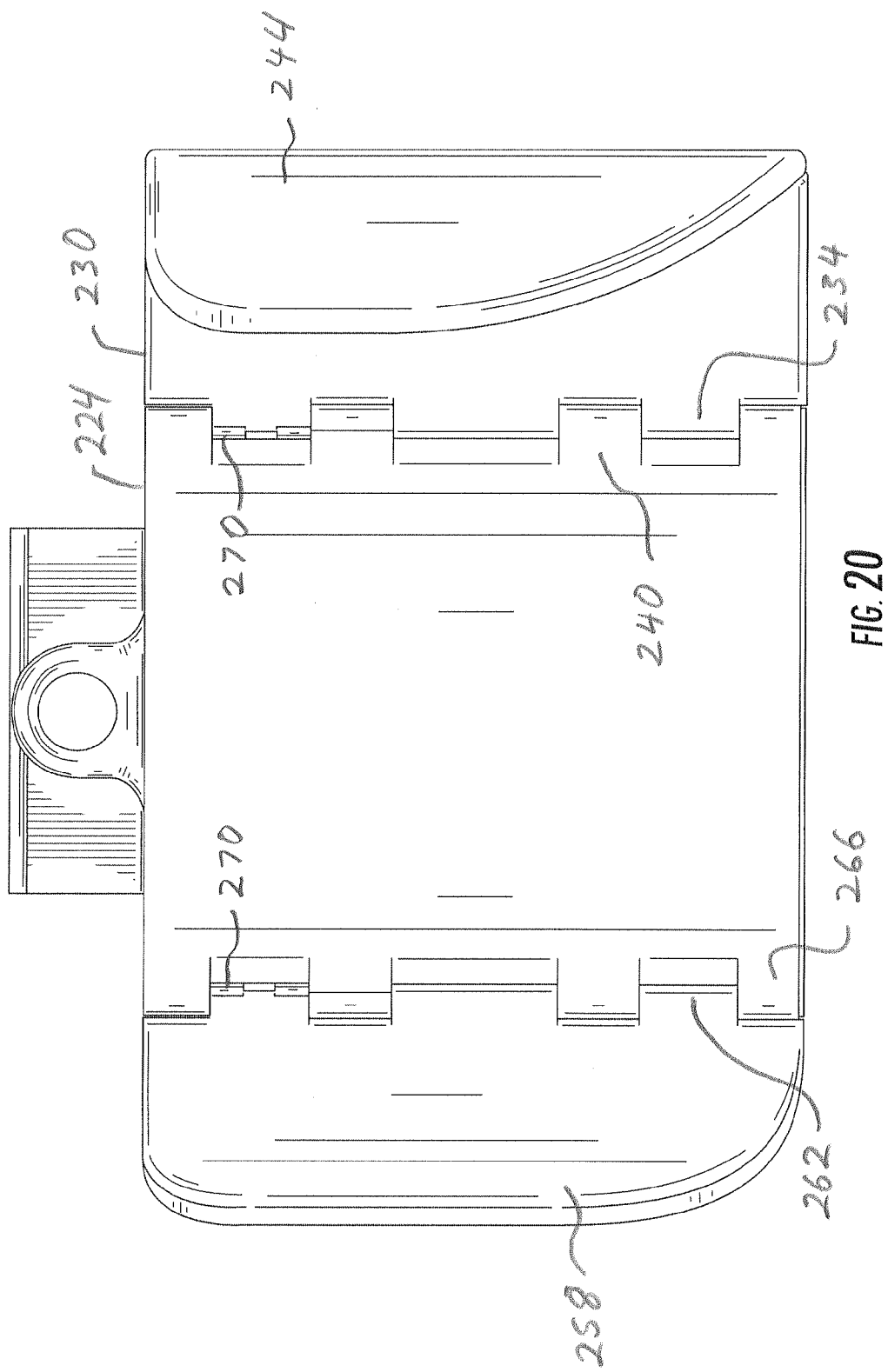
FIG. 20 is a front elevation.
Figure 21:
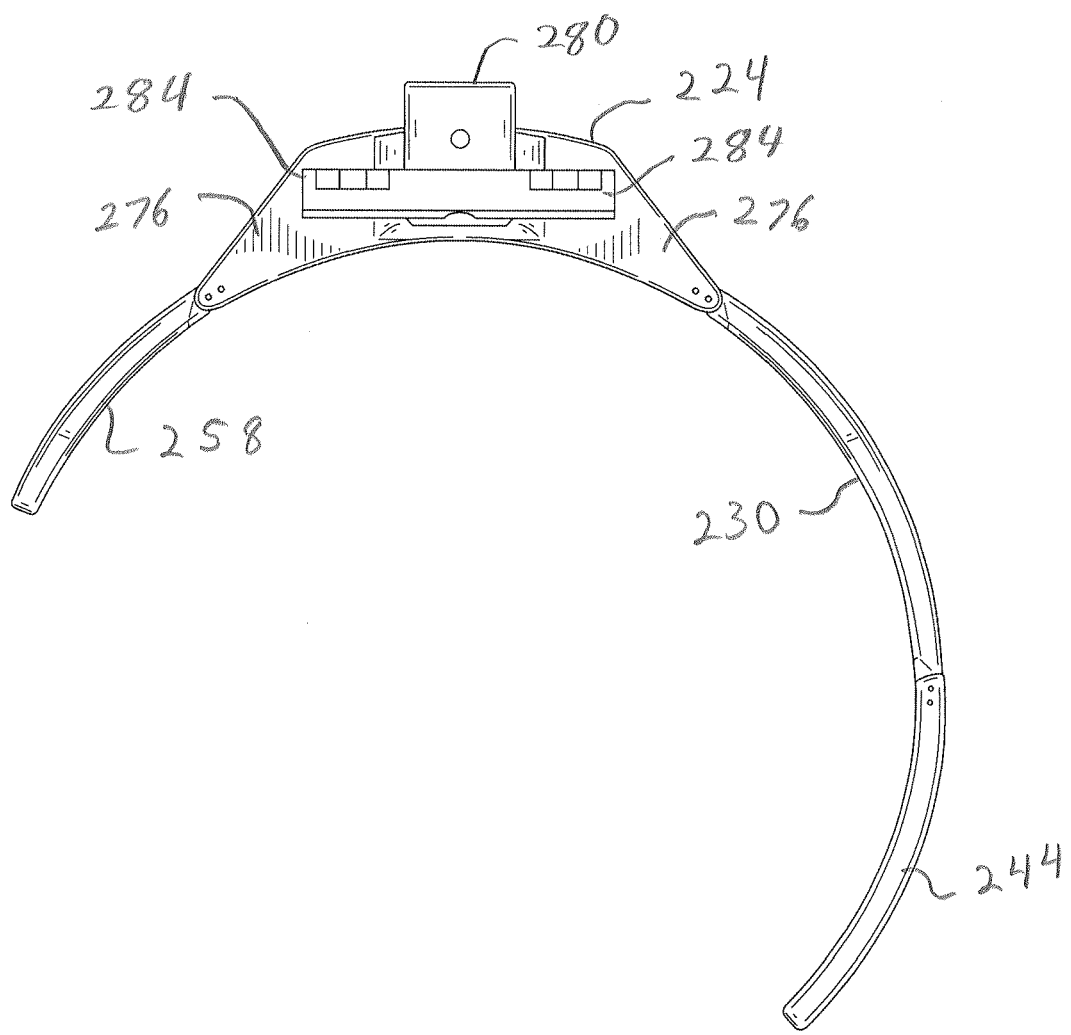
FIG. 21 is a top plan view.

The first blade segment 230, second blade segment 244, and third blade segment 258 are pivotable about the hinged connections from the closed position shown in FIGS. 16-18 to an open position shown in FIGS. 19-21. The closed position is utilized to insert the retractor and blade through an incision or confined opening, and the open position is utilized to retract tissue such as the walls of the atrium. Springs 270 or other suitable structure can be provided to bias the first blade segment 230, second blade segment 244, and third blade segment 258 from the closed to the open position. The springs 270 can be constructed such that the blade segments must be opened manually for a distance in order for the springs to take effect and move the segments the remaining distance to the open position. Other designs are possible in which the blade is integrally attached to the support and the handle. More or fewer blade segments are possible. Structure other than hinges can be provided to allow the blade segments to pivot or otherwise move from the closed to the open position.

Figure 22:
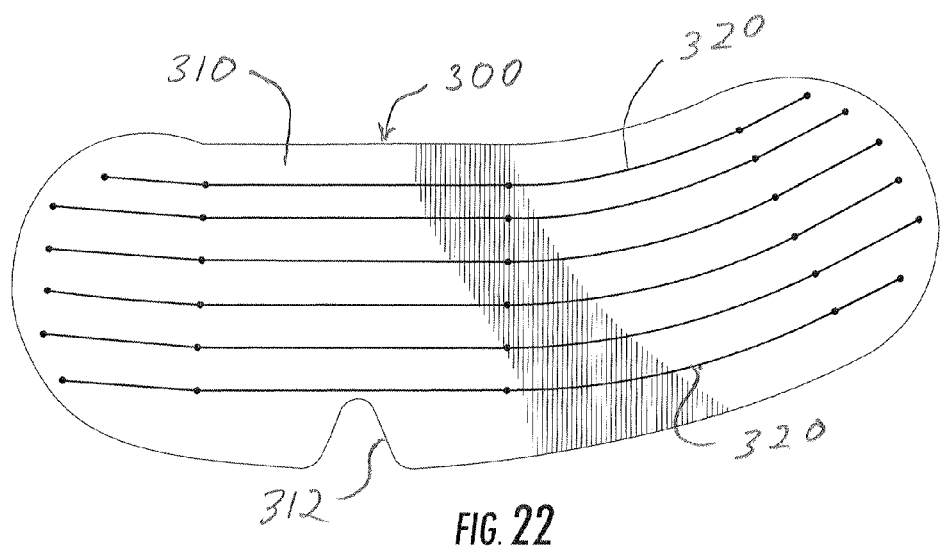
FIG. 22 is a front elevation of a retractor blade according to another embodiment.

Other retractor blade designs are possible. There is shown in FIG. 22 a retractor blade 300 which can have a body 310 formed from a flexible material such as metal or plastic. Strips 320 of a heat sensitive shape memory material such as Nitinol can be attached to or embedded in the body 310. The shape memory material is designed such that at room temperature the retractor blade 300 is in the closed position. Upon the application of heat, the shape memory material takes on a different configuration corresponding to the open configuration of the retractor blade. The heat can be applied by any suitable means, including the application of hot air or gas, passing an electric current through the shape memory material or a nearby electrical conductor so as to heat the shape memory material, or other suitable processes. The blade can vary in size and shape, and can have structure such as notch 312 for mounting the blade 300 on a retractor support.

Figure 23:
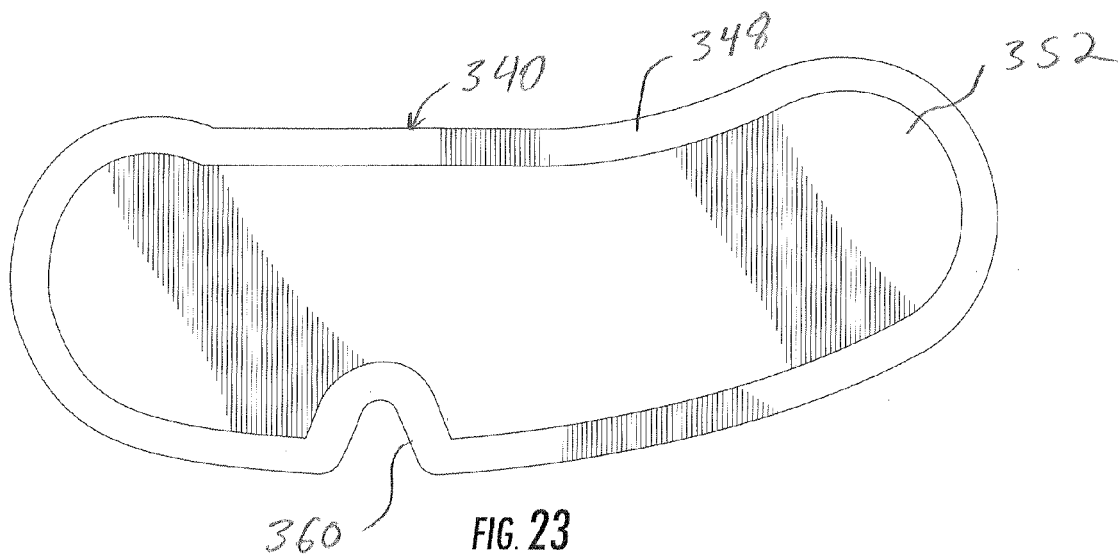
FIG. 23 is a front elevation of a retractor blade according to yet another embodiment.

Another embodiment of a retractor blade incorporating a shape memory material is shown in FIG. 23. The retractor blade 340 can have a body 348. Attached to or embedded in the body 348 is a sheet 352 of shape memory material. The shape memory material is designed such that at room temperature the retractor blade 340 is in the closed position. Upon the application of heat, the sheet 352 of shape memory material takes on a different configuration corresponding to the open configuration of the retractor blade. The blade can vary in size and shape, and can have structure such as notch 360 for mounting the blade 300 on a retractor support. The blade can be made substantially entirely of shape memory material if sharp edges can be avoided which would possibly cut or abrade tissue.

Although the invention has been described in connection with an atrial lift retractor, it will be appreciated that the invention has utility for performing many other types of retractions in other areas of the body. Retractors embodying the invention can take differing configurations, shapes and sizes.

We claim:

1. A retractor, comprising:
a retractor support blade having an inferior face and a superior face;
an elongated unitary flexible retractor blade, having an inferior face and a superior face, said flexible blade having a first, closed position in which ends of the flexible blade are positioned proximal to the support blade and a second, open position in which ends of the flexible blade are positioned distal to the support blade and distal to each other, the flexible blade comprising an elastically deformable material which can be deformed to the closed position and then will expand under its own biasing to the open position;
wherein the flexible blade is detachable from the support blade, the support blade having structure for detachably engaging the flexible blade, with a portion of the superior face of the flexible blade abutting the inferior face of the support blade when the flexible blade is attached to the support blade; and
a handle detachably engaged to and extending from the support blade.

2. The retractor of claim 1, wherein said support blade has a slot for receiving said flexible blade.

3. The retractor of claim 1, wherein said support blade has an engagement surface and said flexible blade has a notch for receiving said engagement surface.

4. The retractor of claim 1, wherein said flexible blade comprises a shape memory material, the shape memory material positioning the flexible blade in the closed position at room temperature, and moving said flexible blade to the open position when said shape memory material is heated.

5. The retractor of claim 4, wherein said flexible blade comprises a blade body and said shape memory material is provided as strips connected to said blade body.

6. The retractor of claim 4, wherein said flexible blade comprises a blade body and said shape memory material is provided as a sheet connected to said blade body.

7. The retractor of claim 1, wherein said support blade and said handle comprise a gas conduit for conducting a gas from the handle to the support blade, said support blade having a gas outlet port for releasing the gas to a surgical site at the support blade.

8. The retractor of claim 1, wherein said flexible blade has a long dimension and a short dimension, said long dimension being at least twice the length of a shorter dimension.

9. The retractor of claim 1, wherein the flexible blade comprises at least one selected from the group consisting of metals and plastics.

10. The retractor of claim 1, wherein the flexible blade has a long dimension with opposing shorter ends, and the structure on the support blade for engaging the flexible blade engages the flexible blade such that, when said flexible blade is in the open position, one of said opposing shorter ends of the flexible blade is closer to the support blade than the other opposing shorter end.

11. The retractor of claim 1, wherein the flexible blade further comprises structure for securing the flexible blade to the support blade.

12. The retractor of claim 11, wherein the structure for securing the flexible blade to the support blade comprises a notch.

13. The retractor of claim 12, wherein the support blade comprises an engagement surface that is cooperatively shaped to engage the notch on the flexible blade.

14. The retractor of claim 11, wherein the structure for securing the flexible blade to the support blade comprises a protrusion.

15. The retractor of claim 14, wherein the support blade comprises structure for engaging the protrusion.

16. The retractor of claim 15, wherein the structure on the support blade for engaging the protrusion comprises flanges, a space defined between the flanges, the protrusion being dimensioned to fit into the space.

17. The retractor of claim 1, wherein the flexible blade comprises structure for securing ends of the flexible blade to one another in a closed position.

18. The retractor of claim 17, wherein the structure for securing the ends of the flexible blade comprises a tab at one of said ends and a cooperating slot at the other of said ends, the tab fitting into the slot to engage one end of the flexible blade to the other end and retain the flexible blade in the closed position.

* * * * *